United States Patent [19]

Young

[11] 4,339,716
[45] Jul. 13, 1982

[54] NUCLEAR MAGNETIC RESONANCE SYSTEMS

[75] Inventor: Ian R. Young, Sunbury-on-Thames, England

[73] Assignee: Picker International Limited, Wembley, England

[21] Appl. No.: 142,130

[22] Filed: Apr. 21, 1980

[30] Foreign Application Priority Data

May 23, 1979 [GB] United Kingdom ............... 7918052

[51] Int. Cl.³ .............................................. G01N 27/00
[52] U.S. Cl. ...................................... 324/309; 324/311
[58] Field of Search ........................ 324/300, 309, 311

[56] References Cited

U.S. PATENT DOCUMENTS

| | | | |
|---|---|---|---|
| 3,474,329 | 10/1969 | Waugh | 324/311 |
| 3,932,805 | 1/1976 | Abe | 324/309 |
| 4,015,196 | 3/1977 | Moore | 324/309 |
| 4,021,726 | 5/1977 | Garroway | 324/309 |
| 4,115,730 | 9/1978 | Mansfield | 324/309 |

FOREIGN PATENT DOCUMENTS 1283915 8/1969 United Kingdom .
1471531 4/1974 United Kingdom .

Primary Examiner—Michael J. Tokar
Attorney, Agent, or Firm—Fleit & Jacobson

[57] ABSTRACT

In a NMR pulse sequence dispersion caused by inhomogeneity in the steady axial magnetic field may be reduced by applying a 180° 'spin-echo' RF pulse. However, whereas it is possible in known pulse sequences to apply a 90° RF pulse in the presence of a selected gradient and to phase correct it adequately, this is not true for the 180° pulse needed in a simple echo system (or the multiple pulses of more complex systems). It has been thought that a 180° pulse could not then be use. It is proposed to apply the 90° $H_1$ pulse in the absence of an axial field gradient. For this purpose it is desirable to apply the RF field and sense the resonance with different coils. The RF coils should be of substantially greater extent in the axial direction than the resonance sensing coils.

9 Claims, 9 Drawing Figures

NUCLEAR MAGNETIC RESONANCE SYSTEMS

The present invention relates to systems for examining distributions of a quantity, in a chosen region of a body, by nuclear magnetic resonance (NMR) techniques.

Practical NMR systems operate by applying suitable combinations of magnetic fields to the body being examined, via magnet (coil) systems, and detecting induced currents in one or more detector coil systems. A suitable sequences of pulsed magnetic fields has been devised to achieve accurate and rapid examination and together with apparatus for implementing it, is described and claimed in U.S. Pat. No. 4,254,778. Further improvements and developments of this procedure and apparatus are described and claimed in U.S. Pat. Nos. 4,309,096 and 4,284,950 and in copending Application Ser. No. 39,650, and the foregoing are hereby incorporated herein by reference.

It is an object of this invention to provide a variation of pulse sequences such as that described in the said application.

According to the invention there is provided a method of examining a body by nuclear magnetic resonance, including the steps of: applying to the body a steady magnetic field along an axis therein; applying an axial magnetic field with a gradient along said axis which, in conjunction with said steady field, gives a predetermined field in a slice of said body; in conjunction with said gradient field, applying a 90° periodic magnetic field pulse, as herein defined, at the Larmor frequency for the field in said slice to cause resonance therein; applying a second axial gradient field 180° displaced in phase from the first and at a proportion of the magnitude thereof to reduce phase dispersion in said slice; applying, at an appropriate stage in the sequence of steps to produce a desired spin-echo, a 180° periodic magnetic field pulse, as herein defined, at said Larmor frequency, wherein the 180° periodic field pulse is applied in the absence of axial field gradients; sensing the resonance signal resulting from resonance in the slice, in the presence of further fields as required; and repeating the step of sensing the resonance signal in the presence of further fields.

The application of the 180° rotating field and subsequent sensing may be repeated several times.

The intial state can be restored by a reversal of the initial steps.

In order that the invention may be clearly understood and readily carried into effect it will now be described, by way of example, with reference to the accompanying drawings, of which, FIG. 1a shows a field pulse sequence for NMR, FIG. 1b shows the effects of the pulses of FIG. 1a on the proton spins vectors, and FIG. 2a shows the field pulse sequence modified for the invention, FIG. 2b shows another form of the sequence of FIG. 2a, FIG. 3 shows a typical NMR examining apparatus, FIG. 4 shows an arrangement of field sensing probes for the apparatus of FIG. 3, FIG. 5 shows in block diagrammatic form a circuit for producing the pulse sequence of FIG. 2.

Figure 1A:
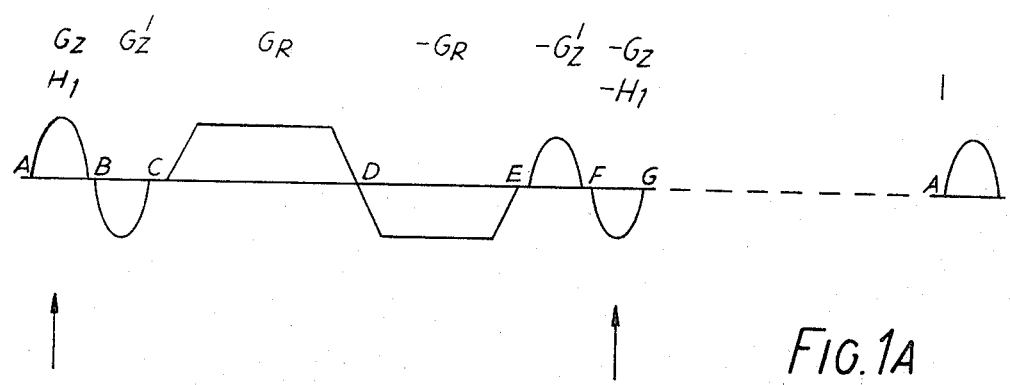

In an NMR system using the pulse sequence of the said application, a steady magnetic field $H_{zo}$ is applied to the body, aligned with an axis (z-axis), all fields in that direction being identified as $H_z$. The nuclear spins then align themselves with that axis. An additional field $H_1$, is the applied; $H_1$ being an R.F. field of frequency related to $H_{zo}$ in a plane normal to $H_{zo}$. This field causes resonance at that frequency so that energy is absorbed in the sample. The resultant spin vectors of nuclei in the body then rotate from the z-axis towards a plane (x,y) orthogonal thereto. The R.F. field is generally applied as a pulse and if $\int H_1 \, dt$ for that pulse is just sufficient to rotate the resultant spin vectors through 90° into the x,y plane then the pulse is termed a 90° pulse. If rotation through 180° is achieved then the pulse is termed a 180° pulse.

On removal of the $H_1$ field the equilibrium alignments re-establish themselves with a time constant $T_1$, the spin-lattice relaxation time. A proportion of the absorbed energy is re-emitted as a signal which can be detected, by suitable sensing coils, at the resonant frequency. This resonance signal decays with a time constant $T_2$ and the emitted energy is a measure of the water content of the body.

As so far described the resonance signal detected relates to the entire body. If individual resonance signals can be determined for elemental samples in a slice or volume of the body then a distribution of a particular nucleus, in effect water content if the chosen nuclei are protons, can be determined for that slice or volume. Additionally or alternatively it is possible to determine a distribution of $T_1$ or $T_2$.

The first step is to ensure that resonance occurs at the chosen frequency substantially only in the selected slice. Since the resonance frequency (the Larmor frequency) is related to the local value of $H_{zo}$, the slice selection is achieved by imposing a gradient on $H_{zo}$ so that the local value of the steady field is of different magnitude in different slices of the body. The steady and uniform $H_{zo}$ field is applied as before. An additional magnetic field gradient $G_z(G_z = \partial H_z/\partial z)$ is also applied. If then the pulsed $H_1$ field is applied at the appropriate frequency, resonance occurs substantially selectively in the slice in which the resonance frequency, as set by the value of $H_{zo}$ and the local value of $G_{zo}$, is equal to the frequency of $H_1$. If the $H_1$ pulse is a 90° pulse, it brings the spin vectors into the x,y plane in the resonant slice. Since the value of the field is only significant during the $H_1$ pulse, it is only necessary that $G_z$ be applied when $H_1$ is applied and in practice $G_z$ is also pulsed. The $H_1$ and $G_z$ fields are therefore then removed. It is still, however, possible to change the resonant frequencies of the spin vectors which are now in the x,y plane. This can be achieved by applying a further field gradient $G_R$ ($G_R = \partial H_z/\partial r$) which is also parallel to $H_{zo}$. The intensity of $G_R$, however, varies from a maximum at an extreme of the slice, through zero (usually but not necessarily in the centre) to a maximum in the reverse direction at the other extreme. Correspondingly the resonant frequencies will vary smoothly across the slice from one side to the other.

As mentioned before, the signal which is now emitted by each nucleus is at the respective resonant frequency. Consequently the signals received from the slice will also have frequencies which vary across the slice in the same manner. The amplitude at each frequency then represents inter-alia, the density of the chosen nucleus in a corresponding strip parallel to the zero plane of $G_R$. The amplitude for each strip can be obtained by varying the detection frequency through the range which occurs across the slice. Prefereably however the total signal at all frequencies is measured. This is then Fourier analysed by well known techniques to give a frequency spectrum. The frequency appropriate to each strip will be known from the field values used and the amplitude for each frequency is given by the spectrum.

As discussed, the individual signals derived from the frequency spectrum, for increments of frequency, correspond to incremental strips parallel to the zero plane of $G_R$. These signals are similar in nature to the so called "edge values" derived and analysed for x-ray beams in computerised tomography. The x-ray edge values are obtained for sets at a plurality of different orientations in an examined slice and then are processed by a suitable method, such as that described in British Pat. No. 1,283,915 and the further development thereof described in British Pat. No. 1,471,531.

It will be apparent that by changing the orientation, relative to the x,y plane, of the zero plane of $G_R$ further sets of signals can be obtained representing proton densities along lines of further sets of parallel lines at corresponding further orientations in the examined slice. The procedure is therefore repeated until sufficient sets of "edge values" have been derived to process by methods like those used for sets of x-ray beams. In practice the $G_R$ field is provided by combination of two fields $G_x$ and $G_y$, which are both parallel to $H_{zo}$ but have gradients in orthogonal directions. The direction of the gradient of the resultant $G_R$ is therefore set by the relative magnitudes of $G_x$ and $G_y$. Other examining methods to which this invention is also applicable replace the r-$\theta$ geometry provided by the rotating $G_R$ gradient with an x-y geometry.

Figure 1B:
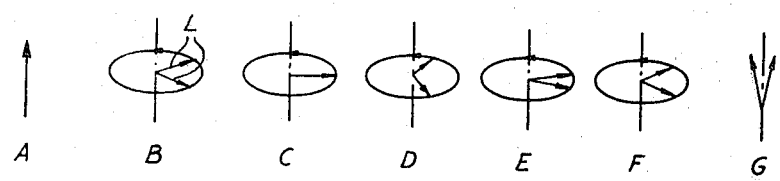

The full examination for one direction of the $G_R$ gradient is achieved by applying, via appropriate coils, the sequence of field pulses shown in FIG. 1a. FIG. 1b shows the effect which each pulse has on the spin vector. It will be realised that the $H_1$ field is a periodic field in effect rotating about the z-axis. In the absence of $H_1$, spin vectors precess about the z-axis. For clarity of explanation the spin vectors are shown in FIG. 1b on a coordinate system which rotates with $H_1$.

Referring to FIG. 1a and 1b together, the pulse cycle comprises six phases, AB to FG, and a recovery period shown by the broken line. The field $H_{zo}$ is continuously present throughout the cycle.

Prior to the first pulse, or after the recovery period if an earlier cycle has been implemented, the mean spin moments are substantially aligned with the z-axis (A).

The field gradient $G_z$ pulse and $H_1$ pulses (AB), simultaneously applied, respectively select the slice and bring the resultant spin moments into the x, y plane (still, of course, precessing about the z-axis). Although the resonant frequency is the same throughout the slice selected, there is a phase dispersion introduced because the excitation occurred in a field gradient. Thus the spin moments are as shown at B, although dispersed between limits much greater than can be conveniently illustrated. Those shown at L are merely indicative of the nature of the dispersion. It has been found that this phase dispersion can be reversed by the application of a negative field gradient pulse, that is a pulse of the correct relative magnitude as $G_z$ but 180° displaced (the relation being typically 55% of the magnitude of $G_z$).

This pulse BC is therefore applied to bring the spin moments in the x y plane into phase as at C. The $H_1$ field need not be continued into the negative gradient pulse ($G_z$).

At that time a signal could be sensed to give proton density for the whole slice. However in this sequence the signal is sensed in the presence of a $G_R$ pulse CD which gives frequency dispersion in a selected direction (R) in the slice as previously described. The change to the new frequencies is almost instantaneous with the application of the $G_R$ pulse and is maintained proportionately throughout the pulse. As discussed the signal is sensed and frequency analysed to give the proton densities for a plurality of parallel relatively displaced strips of the slice. After the $G_R$ pulse the spin moments, which are still largely in the x, y plane despite some relaxation, have a considerable phase dispersion as shown at D (which, as mentioned is merely illustrative since the actual dispersion is n$\pi$ where n exceeds 100). At that stage, if a further cycle as described so far were to be required, it would be necessary to wait for spin-lattice relaxation to realign the spin moments with the z-axis. This could take as much as 5 seconds which, since several hundred cycles are generally required, is much too long.

To return the spin moment substantially back to the starting position (A) the pulse sequence up to D is repeated in the reverse order and reverse sense. Since the $G_R$ pulse is substantially the same as the $G_R$ pulse except for its sense, further signals may be sensed during it. These will be for the same R direction as for the forward pulse and help to improve the signal to noise ratio.

After the reverse pulse sequence the spin moments still show deviation from the z-axis due to phase dispersion caused by spin-spin coupling. This can not be reversed by this pulse sequence nor, it is believed, by any other. The period GA therefore allows some relaxation to thermal equilibrium (time constant $T_1$) which eliminates the effects of the phase dispersion and also reduces the effects of any mismatching between the forward and reverse pulses. Although the relaxation period GA is still necessary, the use of the reversed pulse sequence D to G has much reduced that period and allows faster repetition of the total sequence for other r-directions.

The ratio of period GA to period AG should preferably be approximately the ratio of $T_1$ to $T_2$ for maximum sensitivity. Typically the total period AGA is 40 m sec when AG is approximately 5.5 m sec, AB is 300 $\mu$sec and CD is 2 m sec. The $H_1$ pulse is typically of 0.6 Oe and has a frequency of 4.26 MHz for an $H_{zo}$ of 1000 Oe. All other pulses are at envelope frequency $G_z$ being typically +30 Oe to −30 Oe, $H_R$ being 15 Oe to −15 Oe.

As thus far described the pulse sequence is essentially that described and claimed in the U.S. Ser. No. 41,424.

The length of the signal measurement period CE is determined by the phase dispersion caused by $H_{zo}$ field inhomogeneity and also by the dispersion caused by spin-spin coupling. If the effect of $H_{zo}$ field inhomogeneity is considered to excessively shorten the period CE then it has been proposed that pulse FG may be a 180° r.f. pulse rather than a 90° pulse. Turning the spin moments through 180° produces a so-called "spin-echo" of known form and the $G_R$ pulses similar to CD and DE can be repeated to give a further signal measurement period. The spin-echo procedure is known to reverse the dispersion due to field inhomogeneity and can be repeated here several times until sufficient signal has been obtained or until spin-spin dispersion, which cannot be reversed, becomes excessive. As in the sequence of FIG. 1A, a spin-echo sequence should end with pulses EF, FG and recovery period GA.

If $H_{zo}$ field inhomogeneity is a serious problem the dispersion caused thereby may be reduced by applying a 180° (spin-echo) $H_1$ pulse immediately after the $G_z'$ pulse BC. However, there is a problem associated with the use of spin-echo with this pulse sequence. It is that, whereas it is possible to apply a 90° $H_1$ pulse in the presence of the required selective gradient ($G_z$ or $-G_z$) and to phase correct it adequately ($G_z'$), this is not true for the 180° pulse needed in a simple echo system (or the multiple pulses of complex sequences).

It is therefore proposed any 180° pulses required should be applied in the absence of a $G_z$ gradient. If a spin-echo is required before any signals are sensed, the pulse sequence then becomes, that shown in FIG. 2 in which a 180° $H_1$ pulse CC' is inserted after the $G_z'$ pulse BC. It is not considered necessary to repeat the $H_1(180°)$ pulse in reverse sense at point E to complete the reverse pulse sequence. It may, however, be included at that point if desired.

Figure 2A:
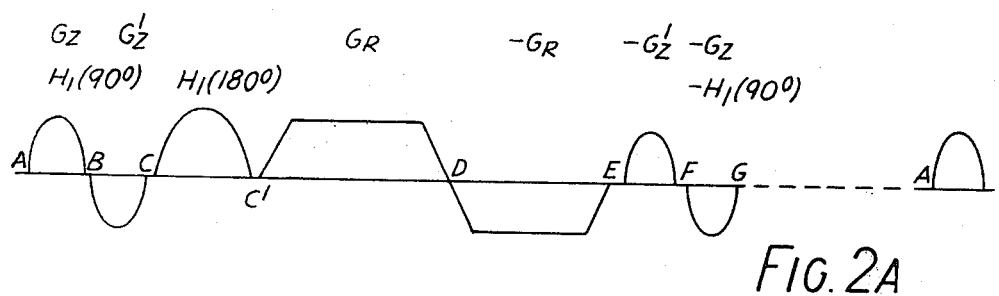
Figure 2B:
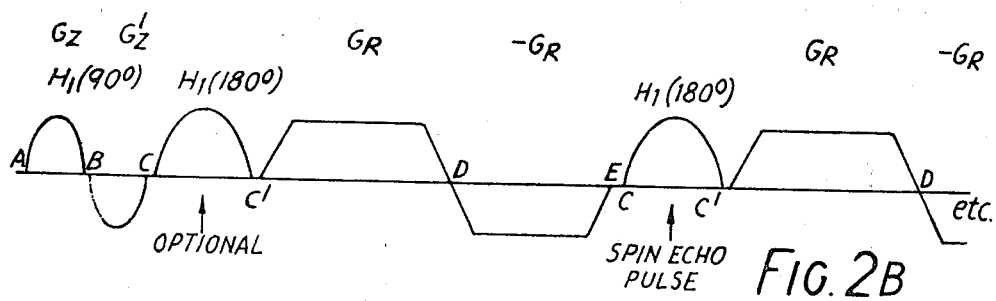

In FIG. 2b there is shown a pulse sequence in which the initial pulse CC' is optional but in which after the $-G_R$ pulse DE there is included a 180° $H_1$ pulse CC' to produce a spin echo, followed by further $G_R$ and $-G_R$ pulses. As mentioned the sequence of $H_1$ (180°), $G_R$, $-G_R$ may be repeated several times and finally terminated with pulses EF, FG and recovery period GA.

Figure 3:
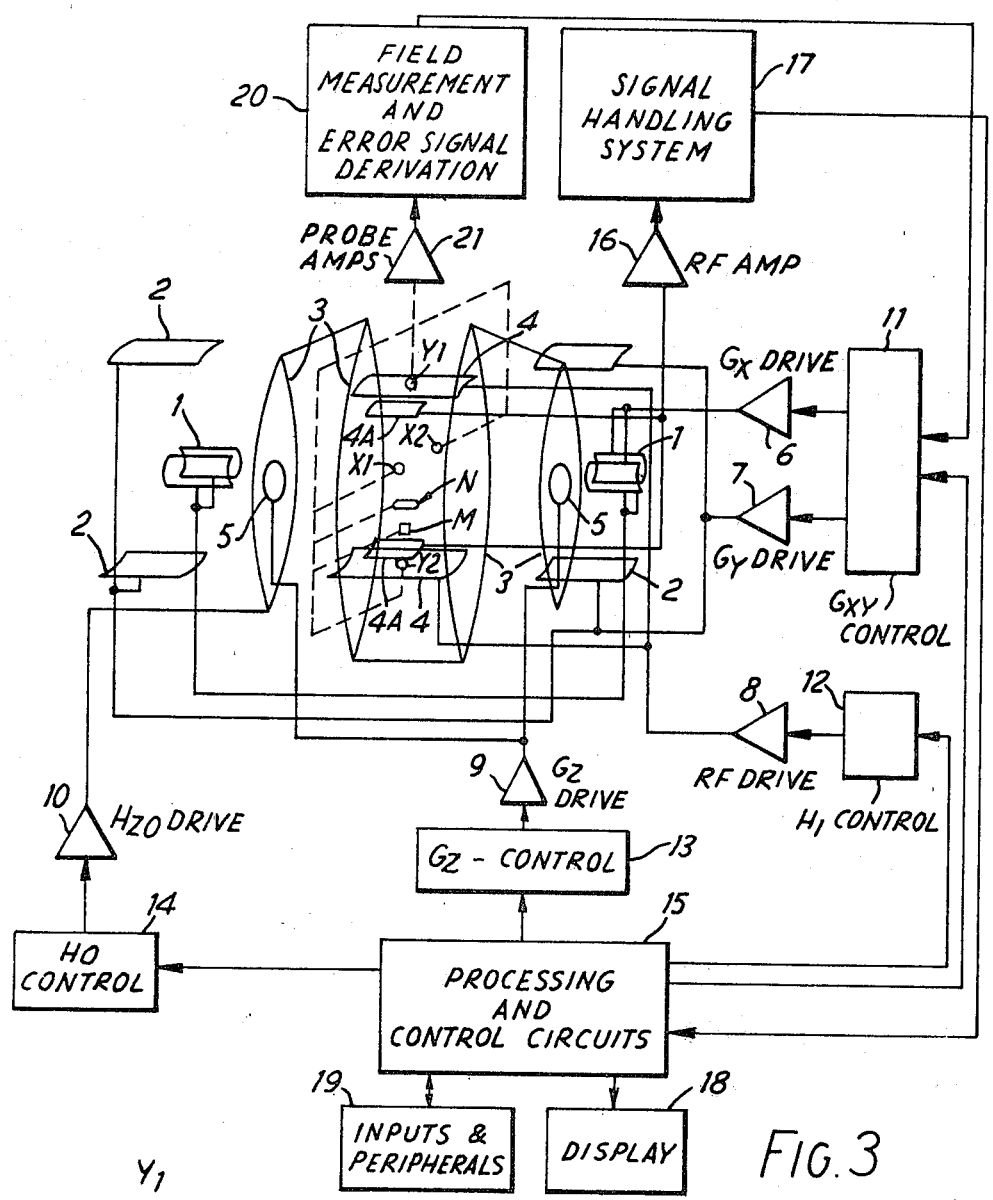

FIG. 3 shows in simplified form a typical imaging NMR apparatus with which the invention can be used. Illustrated schematically are coils 1, which provide the Gx component of $G_R$; 2, which provide the $G_y$ component of $G_R$; 3, which provide the steady $H_{zo}$ field, 4, which provide the rotating $H_1$ RF field, and 5 which provide the Gz field gradient. The coils are driven by Gx, Gy, RF ($H_1$), Gz and $H_{zo}$ drive amplifiers 6, 7, 8, 9 and 10 respectively, controlled by $G_{xy}(G_R)$, $H_1$, $G_z$ and $H_{zo}$ control circuits 11, 12, 13 and 14 respectively. These circuits can take suitable forms which will be well known to those with experience of NMR equipment and other apparatus using coil induced magnetic fields. The circuits are controlled by a central processing and control unit 15 to achieve a desired pulse sequence.

The signal sensed, during the $G_R$ field application, is detected in signal detection coils 4A and is amplified by an RF amplifier 16 before being applied to signal handling circuits 17. The circuits 17 are arranged to make any appropriate calibrations and corrections but essentially transmit the signals, which are effectively proton density values for strips in the body, to the processing circuits to provide the required representation of the examined slice. These circuits can be specially designed to implement the CT type processing as described and claimed in British Pat. No. 1,471,531. It is, however, advantageous to implement the processing by a suitably programmed digital computer. This computer can also conveniently control the pulse sequence and thus represents the circuits indicated at 15. The picture thus obtained is viewed on a suitable display 18, such as a television monitor, and this may include inputs and other peripherals 19 for the provision of commands and instructions to the machine, or other forms of output.

Figure 4:
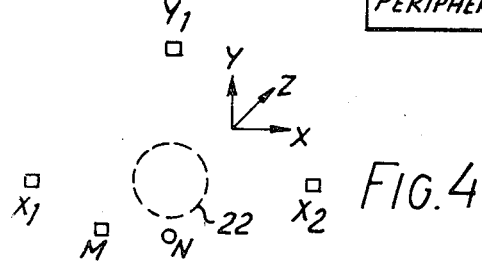

The apparatus also includes field measurement and error signal circuits 20 which receive signals via amplifiers 21 from field probes $X_1$, $X_2$, $Y_1$, $Y_2$, N and M shown. The positions of these probes, in relation to the examined slice of the body 22 of the patient, are shown in FIG. 4. $X_1$, $X_2$, $Y_1$ and $Y_2$ are in this example conventional YIG (Yttrium-iron-garnet) tuned oscillator field measuring probes. Those probes give measures of the fields at the points at which they are situated as oscillations with frequency proportional to the field intensity. The values measured are therefore obtained by a count of oscillations in a set time. In practice, the YIG probes can oscillate in different modes and it is necessary to determine the mode in operation. For this purpose there are provided NMR probes M and N. These probes are simply miniature cells of pure water (such as a closed test tube) surrounded by a small coil. They give a reliable resonance of 4.26 KHz/Oe and can be used to check the YIG tuned oscillator modes. Probe N, fixed in space, acts as a reference. A movable NMR probe M may be moved adjacent the YIG probes in turn to provide data to determine their modes of oscillation, orientation and other characteristics. Alternatively NMR probes may be used in place of the YIG probes exclusively provided the samples therein are sufficiently small, in the direction of the measured field, to give adequate spatial resolution.

The apparatus so far described in relation to FIGS. 3 and 4 is essentially that disclosed in the said co-pending applications.

Figure 5:
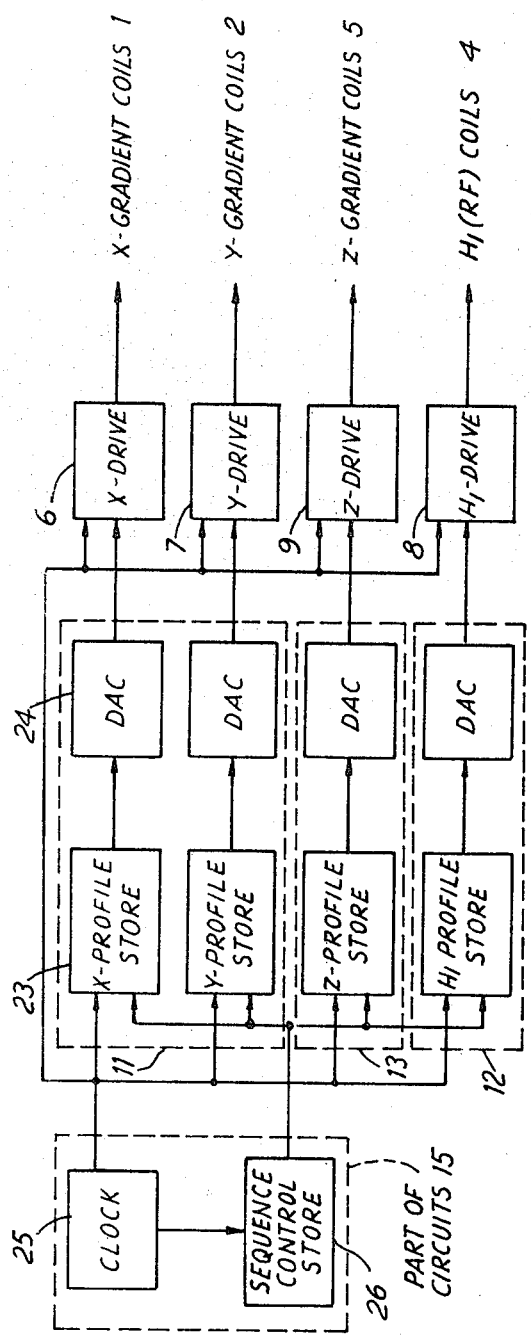

FIG. 5 shows a typical implementation of Gz, Gxy and $H_1$ controls 9, 11 and 12 for controlling a pulse sequence such as that shown in FIG. 1. Four profile stores 23 hold the required shapes for the $G_x$, $G_y$, $G_z$ and $H_1$ pulses in terms of a sequence of current amplitudes and the required duration (in terms of a number of clock pulses) at each amplitude. The specified current at any instant is converted from the digital form in which it is stored to analogue form in digital-to-analogue- converters (DAC's) 24 and the current supplied by one of conventional drive circuits 6 to 9 to the corresponding coil. Timing is by clock pulses from a system clock 25.

The operation of the four profile stores 23 is controlled by a sequence control store 26 which stores the sequence of activation of the profile stores 23 and the duration (in numbers of clock pulses) of operation of each stage of the pulse sequence (including gaps therein). Operation according to this invention is therefore by storing in stores 23 and 26, sequences in which pulse CC' (FIG. 2) is a 180° $H_1$ pulse but with no $G_z$ gradient present.

It should be noted that applying 180° pulses without Gz gradient leaves parts of the body, external to the $H_1$ coil, with the phases not completely reversed and may corrupt the uniformity correction which is the purpose of the process.

The solution to this problem is to use $H_1$ energisation coils substantially (typically 40%) longer than the signal detection coils, which are then relatively insensitive to signals from partly stimulated regions outside the main energisation coils.

Figure 6:
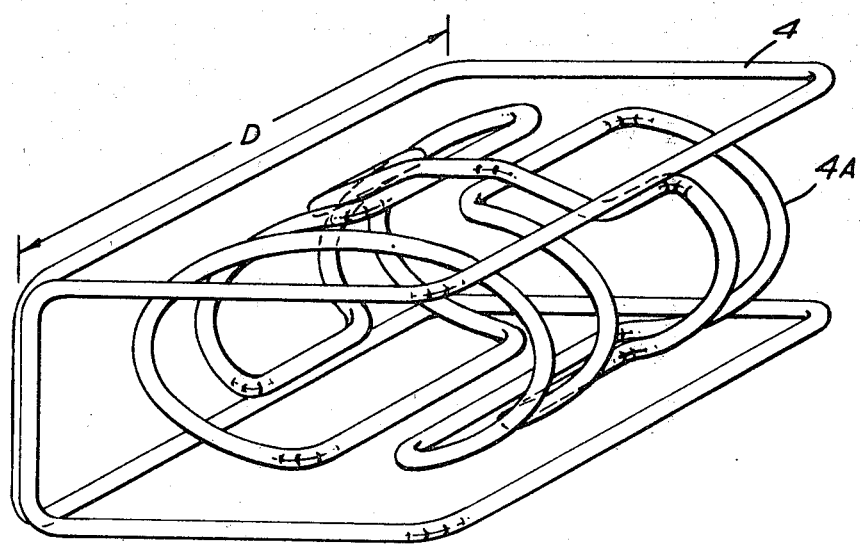
FIG. 6 shows typical drive and sensing coils for a practical apparatus.

FIG. 6 shows a practical arrangement of $H_1$ excitation coils 4 and resonance sensing coils 4A, which were shown only schematically in FIG. 3. "Coils" 4 are rectangular in general shape while coils 4a are saddle shaped. Supports for the coils are not shown but since the coils are of substantial construction, for example ½" to 1" (typically ¾") copper tubing, this presents no problems. Typically the distance D is 20 inches the other dimensions in FIG. 6 being relatively to scale. This gives an effective (not actual) length of coils 4A as being about 10". It should be noted that FIG. 6 is merely illustrative of the general arrangement, not being exactly to scale.

Figure 7:
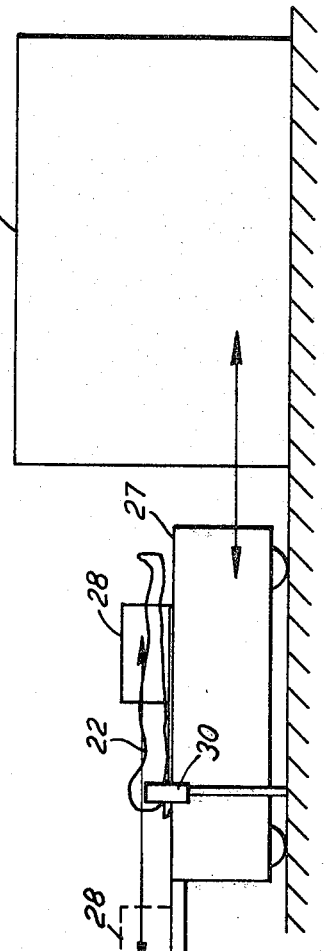
FIG. 7 illustrates the manner of mounting and setting the coils relative to a patient.

For medical examination of a patient the preferred arrangement uses tailored coils mounted on a patient supporting couch or bed shown at 27 in FIG. 7 and changed or moved for examining different parts of the patient. The frame 28 supporting the coils is mounted on wheels on a track 29 and may be aligned over the patient 22 with the couch 27 outside the rest of the apparatus indicated generally at 29. The assembly of couch 27 and coils 4 and 4A (28) is then moved into the rest of the apparatus. It may be moved down it until the coil structure 28 meets an end stop (not shown). This avoids the problems of accurate measurement and location of the patient relative to the structure of the apparatus.

In a preferred example the patient is aligned by a laser 30 which projects say, a vertical line of light on the region to be examined. The laser 30 is a predetermined distance from the examining plane and so the couch is then driven by a stepping motor a predetermined number of counts to place the region to be examined in the examining plane. A number of co-planar sections of the patient may be examined by stepping forward between examining cycles.

Although FIG. 2 shows a spin-echo after pulse BC it should be understood that a spin-echo 180° pulse, in the absence of gradient, may be used at other stages of the pulse sequence. In practice it would be repeated several times in the course of an extended pulse sequence, each time without a z-gradient.

What I claim is:

1. A method of examining a slice of a body by nuclear magnetic resonance, comprising the steps of:
    applying to the body a steady magnetic field along an axis therein;
    applying a first axial gradient magnetic field having a magnitude and having a gradient along said axis which, in conjunction with said steady field, gives a predetermined field in said slice of said body;
    applying, in conjunction with said first axial gradient magnetic field, a first periodic magnetic field pulse at the Larmor frequency for the said predetermined field in said slide to cause resonance therein;
    applying a second axial gradient magnetic field 180° displaced in phase from the first axial gradient magnetic field and at a proportion of the magnitude thereof to reduce phase dispersion in said slice;
    applying, at an appropriate stage in the sequence of steps so as to produce spin-echo, a second periodic magnetic field pulse at said Larmor frequency, wherein the second periodic field pulse is applied in the absence of axial magnetic field gradients; and
    sensing the resonance signal resulting from resonance in the slice, in the presence of further magnetic fields having gradients transverse to said axis.

2. A method according to claim 1, wherein the second periodic magnetic field pulse is applied at least immediately after the first and second axial gradient magnetic fields and before said further magnetic fields.

3. A method according to any one of claims 1 or 2, wherein the second periodic magnetic field pulse is applied after said resonance signal is sensed, and thereafter the resonance signal is again sensed in the presence of said further magnetic fields.

4. A method according to claim 3, wherein the sequence of a second periodic magnetic field pulse followed by sensing in the presence of said further magnetic fields is further repeated at least one time.

5. A method of examining a slice of a body by nuclear magnetic resonance, comprising:
    applying to the body a steady magnetic field along an axis therein;
    applying an axial gradient magnetic field with a gradient along said axis which, in conjunction with said steady field, gives a predetermined field in said slice of said body;
    applying, in conjunction with said gradient field, a first periodic magnetic field pulse at the Larmor frequency for the field in said slice to cause resonance therein; and
    sensing the resonance signal resulting from resonance in the slice, in the presence of magnetic fields having gradients transverse to said axis, wherein there is also included a second periodic magnetic field pulse, at said Larmor frequency effective to produce a spin-echo, the second periodic magnetic field pulse being applied in the absence of axial field gradients.

6. An apparatus for examining a body by nuclear magnetic resonance, the apparatus comprising:
    means for applying to the body a steady magnetic field along an axis therein;
    means for applying to the body an axial gradient magnetic field with a field gradient along said axis;
    means for applying to the body a first periodic magnetic field pulse at a predetermined frequency;
    means for applying to the body a second periodic magnetic field pulse, effective to produce a spin-echo at said predetermined frequency;
    sensing means for sensing a resonance signal resulting from resonance of nuclei in the body caused by said fields;
    means for applying to the body further magnetic fields to control said resonance signal; and
    means for controlling the periodic fields and said gradient field such that the first periodic field pulse is applied in the presence of said gradient field and the second periodic field pulse is applied in the absence of said gradient field.

7. An apparatus according to claim 6, wherein the means for applying the first periodic magnetic field pulse and the means for applying the second periodic magnetic field pulse comprise a first magnetic field coil, and wherein the sensing means includes a second magnetic field coil, the extent of said first magnetic field coil in the direction of said axis being greater than the extent of said second magnetic field coil in the same direction.

8. An apparatus according to claim 7, wherein the extent of the first magnetic field coil in said direction is 40% greater than the extent of the second magnetic field coil in the same direction.

9. An apparatus according to claim 8, including a positioning device on which said body may be supported, said coils being mountable on said positioning device for accurate positioning in relation to said body before said device is introduced to other parts of the apparatus.

* * * * *